(12) United States Patent
Cushman et al.

(10) Patent No.: US 6,362,218 B1
(45) Date of Patent: Mar. 26, 2002

(54) BREFELDIN A DERIVATIVES

(75) Inventors: Mark S. Cushman, West Lafayette; Ankush B. Argade, Indianapolis, both of IN (US); Rudiger D. Haugwitz, Bethesda, MD (US); Rajesh Devraj, Ballwin, MO (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/581,773

(22) PCT Filed: Dec. 18, 1998

(86) PCT No.: PCT/US98/27000

§ 371 Date: Jun. 16, 2000

§ 102(e) Date: Jun. 16, 2000

(87) PCT Pub. No.: WO99/31084

PCT Pub. Date: Jun. 24, 1999

Related U.S. Application Data

(60) Provisional application No. 60/068,030, filed on Dec. 18, 1997.

(51) Int. Cl.[7] .................... A61K 31/365; C07D 313/00; C07D 493/00
(52) U.S. Cl. ................ 514/450; 549/270; 549/271
(58) Field of Search .................... 514/450; 549/270, 549/271

(56) References Cited

U.S. PATENT DOCUMENTS 4,608,078 A    8/1986    Acker

FOREIGN PATENT DOCUMENTS

| WO | WO 94/17056 | 8/1994 |
|----|-------------|--------|
| WO | WO 96/00726 | 1/1996 |
| WO | WO 96/40112 | 12/1996 |

OTHER PUBLICATIONS

Hori, Hitoshi et al., "Synthesis and Activity of Brefeldin A Analogs As Inducers of Cancer Cell Differentiation And Apoptosis", *Bioorganic & Medicinal Chemistry Letters*, vol. 7, No. 2. , pp. 139–144, (1997).

Stahelin, L. Andrew et al., "7–Dehydrobrefeldin A, a Naturally Occuring Brefeldin A Derivative, Inhibits Secretion and Causes a cis–to–trans Breakdown to Golgi Stacks in Plant Cells[1]", *Plant Physiol.*, 113, pp. 487–492, (1997).

Proksa, B. et al., "Oxidation of brefeldin A", *Institute of Chemistry*, Slovak Academy of Sciences, and Department of Biochemical Technology, Pharmazie 47, pp. 582–584, (1992).

Freirich et al., "Quantitative Comparison of Toxicity of Anticancer Agents in Mouse, Hamster, Dog, Monkey, and Man.", *Cancer Chemotherapy Reports*, vol. 50, No. 4 pp. 219–244 (1966).

*Primary Examiner*—T. A. Solola
(74) *Attorney, Agent, or Firm*—Barnes & Thornburg

(57) ABSTRACT

Cytotoxic Michael addition derivatives of brefeldin A are described. Oxidation of thiol addition products of brefeldin A provides the corresponding sulfoxides and sulfones. The sulfoxides exhibited more cytotoxic activity than the corresponding sulfides and sulfones in a variety of human cancer cell lines. Pharmaceutical formulations of the disclosed cytotoxic derivatives are also described.

8 Claims, No Drawings

BREFELDIN A DERIVATIVES

CROSS-REFERENCE TO RELATED APPLICATIONS

This application is a U.S. national application of internatinal application serial No. PCT/US98/27000 filed Dec. 18, 1998, which claims priority to U.S. provisional application serial No. 60/0680,030 filed Dec. 18, 1997.

GOVERNMENT RIGHTS

Research relating to this invention was supported in part by the U.S. Government under Grant No. N01-CN-67260 awarded from the National Insitute of Health. The U.S. Government may have certain rights in this invention.

FIELD OF INVENTION

This invention relates to novel cytotoxic macrolide compounds. More particularly, this invention is directed to derivatives of brefeldin A, pharmaceutical formulations comprising said derivatives, and a method of using certain of those derivatives as brefeldin A prodrugs.

BACKGROUND AND SUMMARY OF THE INVENTION

Brefeldin A is a macrolide antibiotic first isolated from the fungus *Penicillium decumbers*. The bicyclic ring structure was subsequently established by X-ray crystallography. Brefeldin A possesses a number of biological properties of potential therapeutic interest, including antitumor, antiviral, antifungal, nematocidal, and antimitotic effects. Mode of action studies have revealed that brefeldin A inhibits protein transport from the endoplasmic reticulum to the Golgi apparatus, causes reversible disassembly of the Golgi complex, and blocks protein transport beyond the Golgi complex. Recently, it has been shown that brefeldin A induces DNA fragmentation that is associated with apoptosis in cancer cells. This recent discovery has stimulated a great deal of interest in the preclinical development of brefeldin A as an anticancer agent.

Clinical use of brefeldin A is severely limited by certain of its pharmacokinetic properties; negligible bioavailability after oral administration, and rapid clearance from the blood plasma after intravenous administration. Studies in Chinese hamster ovary cells have indicated that brefeldin A is secreted as glutathione and cysteine conjugates. Studies have also revealed that glutathione-S-transferase system may be responsible for the inactivation of brefeldin A in mammalian cells.

Formulation of brefeldin A is also complicated by its low solubility in aqueous solutions. Despite the existence of the lactone system and two hydroxyl groups on its bicyclic ring system, brefeldin A is only marginally soluble in aqueous medium. This severely limits the formulation of brefeldin A in solution for intravenous or intramuscular injection.

In accordance with this invention cytotoxic derivatives of brefeldin A having increased solubility and apparent prodrug activity have been prepared. Thus in accordance with one embodiment of this invention there is provided a compound of formula

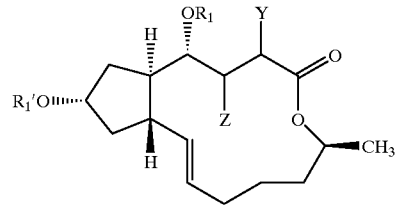

I wherein $R_1$ and $R_1'$ are independently hydrogen or carboxy substituted $C_1$–$C_5$ alkanoyl, Y is H or OH, and Z is OH or —S(O)$_n$R wherein n is 0, 1 or 2 and wherein R is $C_1$–$C_6$ alkyl, phenyl, or $C_1$–$C_6$ alkyl or phenyl substituted with one or more groups selected from the group consisting of OH, $C_1$–$C_4$ alkoxy, halo, carboxy, carbo($C_1$–$C_4$ alkoxy), amino, —SO$_3$H, and mono or di ($C_1$–$C_4$ alkyl)amino, provided that when n is 0, R is not a 2-amino-2-carboxy alkyl group or an acylated derivative thereof, and provided that when Y is OH, Z is OH. The compounds of formula I wherein n is 0, 1, or 2 represent the corresponding sulfides, sulfoxide and sulfones, respectively.

This invention also directed to a method for preparing compounds of formula I by reacting brefeldin A, or a derivative thereof, with a thiol of the formula RSH to produce a compound of formula I wherein n is 0. The corresponding compounds wherein n is 1 or 2 are prepared by oxidizing the sulfide intermediates (n=O). In addition, brefeldin A and its derivatives can be optionally reacted with a $C_1$–$C_6$ cyclic anhydride to form a compounds of formula I wherein at least one of $R_1$ and $R_1'$ is carboxy substituted $C_1$–$C_5$ alkanoyl.

In yet another embodiment of this invention there is provided a method for providing therapeutically effective serum levels of brefeldin A in a patient in need of the therapeutic benefit of brefeldin A by administering an effective amount of a compound of formula 1 wherein n is 0 or 1 in a pharmaceutically acceptable carrier.

The present invention further provides pharmaceutical formulations comprising an effective amount of the brefeldin A derivatives for treating a patient having a tumor or other neoplastic disease. As used herein, an effective amount of the brefeldin A derivative defined as the amount of the compound which, upon administration to a patient, inhibits growth of tumor cells, kills malignant cells, reduces the volume or size of the tumors or eliminates the tumor entirely in the treated patient.

The effective amount to be administered to a patient is typically based on body surface area, patient weight, and patient condition. The interrelationship of dosages for animals and humans (based on milligrams per meter squared of body surface) is described by Freireich, E. J., et al., *Cancer Chemother. Rep.*, 50 (4): 219 (1966). Body surface area may be approximately determined from patient height and weight (see e.g., Scientific Tables, Geigy Pharmaceuticals, Ardley, New York, pages 537–538 (1970)). An effective amount of the brefeldin A derivative in the present invention can range from about 5 mg/kg to about 100 mg/kg, more preferably from about 0.25 mg/kg to about 50 mg/kg, and most preferably about 0.1 to about 10 mg/kg.

Effective doses will also vary, as recognized by those skilled in the art, dependant on route of administration, excipient usage and the possibility of co-usage with other therapeutic treatments including other anti-tumor agents, and radiation therapy.

The pharmaceutical formulation may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable liquid carrier. In one preferred aspect of the present embodiment, the brefeldin A derivative is dissolved in a saline solution containing 5% of dinmethyl sulfoxide and 10% Cremphor EL (Sigma Chemical Company). Additional solubilizing agents such as cyclodextrins, which form specific, more soluble complexes with the present compounds, or other solubilizing agents well-known to those familiar with the art, can be utilized as pharmaceutical excipients for delivery of the present compounds.

The present compound can also be formulated into dosage forms for other routes of administration utilizing well-known methods. The pharmaceutical compositions can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with conventional procedure by compressing mixtures of the active brefeldin A derivatives and solid carriers, and lubricants well-known to those familiar with the art. Examples of solid carriers include starch, sugar, bentonite. The compounds of the present invention can also be administered in a form of a hard shell tablet or capsule containing, for example, lactose or mannitol as a binder and conventional fillers and tableting agents.

The following description is provided to illustrate various embodiments of Applicants' invention, and are not intended to in any way limit the scope of the invention as set forth in this specification and appended claims.

DETAILED DESCRIPTION OF THE INVENTION

Brefeldin A is a macrolide antibiotic first isolated from the fungus *Penicillium decumbens*. The structure 1 was subsequently established by X-ray crystallography. It has been known for a long time that brefeldin A possesses a number of interesting biological properties of potential therapeutic interest, including antitumor, antiviral, antifungal, nematocidal, and antimitotic effects. Studies of the mode of action of brefeldin A have revealed that it inhibits protein transport from the endoplasmic reticulum to the Golgi apparatus, causes reversible disassembly of the Golgi complex, and blocks protein transport beyond the Golgi complex. In addition, the ability of brefeldin A to induce DNA fragmentation associated with apoptosis in cancer cells has stimulated a great deal of recent interest in its preclinical development as an anticancer agent. However, the potential clinical use of brefeldin A is severely limited by its undesirable pharmacokinetic properties, including negligible bioavailability after oral administration and rapid clearance from the blood plasma after intravenous administration. Formulation of brefeldin A is also complicated by its low aqueous solubility. In view of these problems, additional work in the area of brefeldin A congener and prodrug synthesis is indicated.

Brefeldin A prodrugs would ideally be water soluble compounds which would be readily absorbed after oral administration and would be metabolized back to brefeldin A after systemic distribution in the blood plasma. The Michael addition of thiols to the α,β-unsaturated lactone system present in brefeldin A has been investigated. The resulting sulfides might then be metabolized to sulfoxides after absorption, and the sulfoxides could then conceivably undergo syn elimination back to the α,β-unsaturated lactone system present in brefeldin A. In accordance with this invention, a variety of thiols have been reacted with brefeldin A, and the resulting sulfides have ben oxidized to sulfoxides/sulfones. The cytotoxicities of the resulting compound have been investigated in human cancer cell cultures.

Thiol addition products 2–12 were prepared by reacting brefeldin A with the corresponding thiols in ethanol in the presence of "proton sponge®" [1,8-bis(dimethylamino) naphthalene]. The reactions occurred readily and were found to be highly diastereoselective. The R configuration at C-3 in these products was assigned on the basis of the X-ray structure of a crystalline bis(3,5-dinitrobenzoate) derivative of the adduct formed from brefeldin A and 2-mercaptoethanol. The X-ray and NMR data indicate that there is a conformational change in the macrocycle in going from brefeldin A to the adducts. In brefeldin A, C-2 and C-5 are anti, whereas in the products, they are gauche. The specific thiol addition products prepared were chosen to incorporate a variety of polar, acidic, and basic functional groups that would impart additional aqueous solubility. Compounds 11 and 12 were synthesized because studies in Chinese hamster ovary cells have indicated that brefeldin A is secreted as these glutathione and cysteine conjugates. The biological activities of these two compounds is of interest because of the possibility that the glutathione-S-transferase system is responsible for the inactivation of the antibiotic in mammalian cells. Nine of the sulfides were oxidized to the corresponding sulfoxides 13–21.

Certain mono- and diesters of brefeldin A with polar groups in the side chain were synthesized by the reaction of brefeldin A with succinic anhydride and glutaric anhydride. These succinate and glutarate derivatives might also act as brefeldin A prodrugs and be hydrolyzed back to brefeldin A by esterases present in the blood plasma. The monosuccinate 22 of brefeldin A was obtained by the reaction of 1 with 1.5 equivalents of succinic anhydride in pyridine at 60° C. However, when glutaric anhydride was employed using this method, there was no product formation. In order to force the reaction, 4-dimethylaminopyridine was added to the reaction mixture. This led to the formation of both the monoester 23 and the diester 25 along with unreacted starting material. The diester 25 could be separated from the mixture

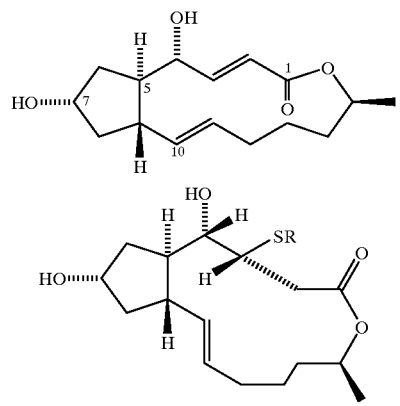

-continued

2 R = CH₂CH₂COOCH₃
3 R = p-C₆H₄OH
4 R = CH₂CH₂N(CH₃)₂
5 R = CH₂CH₂OH
6 R = CH₂COOH
7 R = CH₂COOCH₃
8 R = CH₂CH(OH)CH₂OH
9 R = CH₂CH₂NH₂
10 R = p-C₆H₄OCH₃
11 R = CH₂CH(NH₂)COOH
12 R = CH₂CHNHCOCH₂CH₂CH(NH₂)COOH
          |
          CONHCH₂COOH

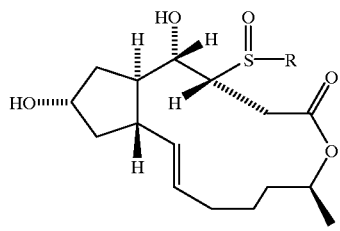

13 R = CH₂CH₂COOCH₃
14 R = p-C₆H₄OH
15 R = CH₂CH₂OH
16 R = CH₂COOCH₃
17 R = CH₂CH(OH)CH₂OH
18 R = CH₂CH₂NH₂
19 R = p-C₆H₄OCH₃
20 R = CH₂CH₂N(CH₃)₂
21 R = CH₂CH(NH₂)COOH

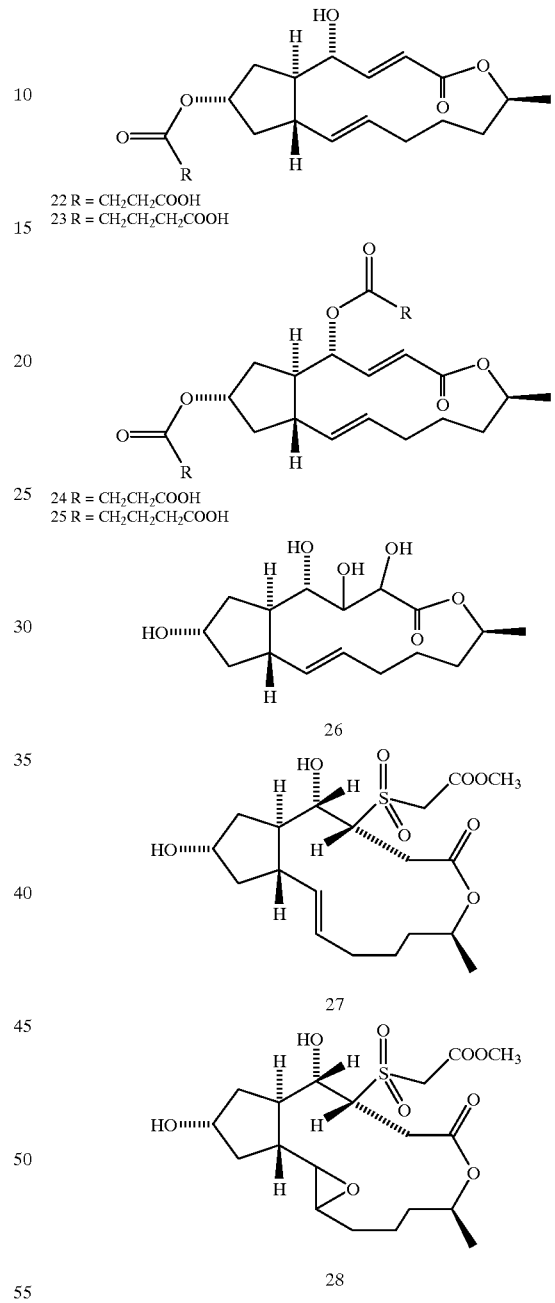

22 R = CH₂CH₂COOH
23 R = CH₂CH₂CH₂COOH

24 R = CH₂CH₂COOH
25 R = CH₂CH₂CH₂COOH

26

27

28 by column chromatography on silica gel, but the monoester 23 co-eluted with some impurities and brefeldin A. The reaction was repeated again with 3 equivalents of glutaric anhydride and 2 equivalents of DMAP to afford the desired diester 25 as the major product. A single recrystallization from hexanes and ethyl acetate afforded a pure sample of the diglutarate 25. This method was then applied to the synthesis of the disuccinate 24 of brefeldin A. Reaction of 1 with 3 equivalents of succinic anhydride in the presence of 2 equivalents of 4-dimethylaminopyridine in pyridine at 60° C. afforded the desired compound 24 in moderate yield after column chromatographic purification on silica gel and recrystallization.

In order to synthesize and isolate the monoglutarate 23 in pure form, the reaction was attempted in pyridine as the solvent. Since addition of 4-dimethylaminopyridine causes the formation of the diester 25 and the reaction does not occur at 60° C., the reaction temperature was raised to 110° C. for 36 hours and 4-dimethylaminopyridine was omitted. The TLC of the reaction mixture indicated the formation of the monoglutarate 23 as the major product along with some unreacted starting material. A very minor amount of the undesired diester 25 was also present. Column chromatography on silica gel followed by recrystallization from diethyl ether and hexanes afforded the desired compound 23.

An attempt was also made to introduce additional hydroxyl groups into the brefeldin A system in order to increase aqueous solubility and to provide additional structure-activity information. To this end, the reaction of brefeldin A with osmium tetroxide was investigated. Thus, the reaction of (+)-brefeldin A with two equivalents of N-methylmorpholine oxide (NMO) and a catalytic amount of osmium tetraoxide ($OsO_4$) in a mixture of t-BuOH:$H_2O$ was attempted at room temperature. After 4 hours stirring at room temperature the formation of a product was observed on TLC. After usual work up and purification, the dihydroxylation product 26 was isolated in 89% yield. $^1$H NMR analysis of the reaction product 26 showed disappearance of C-2 and C-3 olefinic protons from 1 and presence of C-10 and C-11 olefinic protons, indicating a regioselective dihydroxylation. The stereochemistry of the dihydroxylation product 26 at C-2 and C-3 has not been determined.

Some attention has also been directed toward the determination of the structures of the reaction products obtained from the oxidation of the methyl thioglycolate addition product 7 under forcing conditions. The oxidation of 7 with 1.1 equivalents of m-chloroperbenzoic acid in methylene chloride at 0° C. for 2 minutes afforded the corresponding sulfoxide 16 in good yield. However, the treatment of sulfide 7 with 2.2 equivalents of m-chloroperbenzoic acid in methylene chloride at room temperature for 4 hours gave the desired sulfone 27 in 46% isolated yield. When the sulfide 7 was treated with 4.4 equivalents of m-chloroperbenzoic acid in methylene chloride for 7 hours, the sulfur was oxidized to the sulfone and the C-10, C-11 double bond was also oxidized, resulting in compound 28. The stereochemistry of the epoxide has not yet been determined.

The new synthesized brefeldin A prodrug candidates and analogs were examined for antiproliferative activity against human cancer cell lines in the National Cancer Institute screen, in which the activity of each compound was evaluated with approximately 55 different cancer cell lines of diverse tumor origins. The GI50 values obtained with selected cell lines, along with the mean graph midpoint (MGM) values, are summarized in Table 1. The MGM is based on a calculation of the average GI50 for all of the cell lines tested (approximately 55) in which GI50 values below and above the test range ($10^{-4}$ to $10^{-8}$ molar) are taken as the minimum ($10^{-8}$ molar) and maximum ($10^{-4}$ molar) drug concentrations used in the screening test.

It is apparent from the data in Table 1 as well as from the more extensive data in approximately 55 cell lines (data not shown) that neither brefeldin A nor any of the new derivatives prepared in the present study have significant selectivity for any particular subpanel of cancer cell lines. It is also clear that the sulfide derivatives 2–12 (MGM 0.37–42 $\mu$M) are in general much less active that brefeldin A (MGM 0.040 $\mu$M). The α,β-unsaturated lactone moiety therefore appears to be an important structural determinant for cytotoxicity. This point is also borne out by the cytotoxic activity of 26 (MGM 3.0 $\mu$M) relative to 1 (MGM 0.041 $\mu$M), and it is also consistent with a recent report documenting the importance of the α,β-unsaturated lactone moiety for induction of apoptotic DNA fragmentation.

The more active of the sulfide derivatives were 12 (MGM 0.37 $\mu$M), 4 (MGM 0.68 $\mu$M), 11 (MGM 1.8 $\mu$M), and 9 (MGM 2.5 $\mu$M). It is worth noting that all of these more active sulfides have side chains containing basic amino groups that could possibly catalyze the elimination of the sulfide to regenerate brefeldin A.

TABLE 1

Cytotoxicities of Brefeldin A Analogs cytotoxicity (GI50 in $\mu$M)[a]

| compd no. | Lung HOP-62 | Colon HCT-116 | CNS SF-539 | Melanoma UACC-62 | Ovarian OVCAR-3 | Renal SN12C | Prostate DU-145 | Breast MDA-MB-435 | MGM[b] |
|---|---|---|---|---|---|---|---|---|---|
| 1 | 0.070 | 0.029 | 0.040 | 0.022 | 0.032 | 0.090 | 0.13 | 0.041 | 0.040 |
| 2 | 5.8 | 2.0 | 3.5 | 4.7 | 2.7 | 6.6 | 24 | 3.6 | 4.1 |
| 3 | 3.2 | 2.5 | 5.1 | 4.8 | 2.4 | 4.4 | 6.3 | 3.3 | 3.2 |
| 4 | 0.54 | 0.75 | 0.39 | 0.43 | 0.54 | 1.40 | 2.4 | 0.50 | 0.68 |
| 5 | 34 | 19 | 23 | 40 | 27 | 33 | 30 | 34 | 20 |
| 6 | 30 | 23 | 34 | 33 | 30 | 39 | 38 | 42 | 33 |
| 7 | 28 | 19 | 24 | 6.8 | 27 | 32 | 30 | 30 | 17 |
| 8 | 33 | 36 | 32 | 16 | 22 | 34 | 18 | 36 | 23 |
| 9 | 3.9 | 3.5 | 4.9 | 2.7 | 2.2 | — | — | 3.3 | 2.5 |
| 10 | 24 | 33 | 26 | 29 | 22 | 30 | 36 | 19 | 31 |
| 11 | 3.8 | 2.6 | 2.4 | 2.4 | 1.5 | 3.5 | 3.5 | 1.0 | 1.8 |
| 12 | 0.87 | 0.24 | 0.42 | 0.28 | 0.29 | 0.55 | 2.48 | 0.52 | 0.49 |
| 13 | 0.40 | 0.32 | 0.41 | 0.083 | 0.20 | 0.61 | 0.45 | 0.29 | 0.35 |
| 14 | 0.088 | 0.026 | 0.017 | 0.030 | 0.025 | 0.050 | 0.118 | 0.042 | 0.037 |
| 15 | 0.29 | 0.21 | 0.058 | 0.064 | 0.19 | 0.65 | 0.26 | 0.090 | 0.11 |
| 16 | 0.44 | 0.48 | 0.38 | 0.24 | 0.27 | 1.46 | 1.25 | 0.39 | 0.68 |
| 17 | 0.37 | 0.26 | 0.19 | 0.24 | 0.22 | 0.36 | 0.88 | 0.38 | 0.28 |
| 18 | 0.15 | 0.086 | 0.020 | 0.021 | 0.082 | 0.12 | 0.17 | 0.055 | 0.055 |
| 19 | 0.49 | 0.65 | 0.41 | 0.32 | 0.25 | - | — | 0.42 | 0.41 |
| 20 | 0.35 | 0.28 | 0.30 | 0.071 | 0.14 | 0.15 | 0.48 | 0.41 | 0.20 |
| 21 | 0.70 | 0.091 | 0.038 | 0.038 | 0.039 | 0.16 | 0.43 | 0.050 | 0.096 |
| 22 | 3.4 | 17 | 0.54 | 1.9 | 3.3 | 4.3 | 6.8 | 1.1 | 2.5 |
| 23 | 33 | 21 | 22 | — | 20 | 32 | 30 | 11 | 13 |
| 24 | >100 | >100 | >100 | >100 | >100 | >100 | >100 | >100 | 89 |
| 25 | >100 | >100 | >100 | >100 | >100 | >100 | >100 | >100 | 98 |
| 26 | 5.0 | 3.4 | 0.68 | 1.6 | 2.4 | 2.7 | 6.7 | 3.8 | 2.3 |
| 27 | 5.1 | 3.7 | — | 5.0 | 3.2 | 3.3 | 6.0 | 5.5 | 3.5 |
| 28 | 54 | 37 | 38 | 53 | 25 | 28 | 70 | 38 | 31 |

[a]The cytotoxicity $GI_{50}$ values are the concentrations corresponding to 50% growth inhibition.
[b]Mean graph midpoint for growth inhibition of all human cancer cell lines successfully tested.

Included in this list are the brefeldin A secondary metabolites 11 and 12, assuming the metabolites in fact have the same configuration as the major thiol addition products.

Turning to the sulfoxides 13–21, it is evident that these compounds are the most active set investigated, with MGM values ranging from 0.037 $\mu$M for compound 14 to 0.68 $\mu$M for compound 16. The cytotoxicity of 14 is essentially equipotant with that of brefeldin A (MGM 0.040 $\mu$M). The average MGM value for the set of sulfoxides 13–21 is 0.24 $\mu$M, which is much lower than the 14 $\mu$M value calculated for the sulfides 2–12. It seems likely that the sulfoxides undergo elimination during cytotoxicity testing and that the observed biological results are at least in part due to the presence of brefeldin A. This would account for the difference in activity seen between the sulfides and sulfoxides.

In order to investigate the proposed sulfoxide elimination reaction to regenerate brefeldin A, compounds 13, 15, and 20 were placed in a $D_2O/CD_3OD$ buffer, pH 7.4, containing sodium bicarbonate and sodium acetate at room temperature and the $^1H$ NMR spectra were recorded at various intervals. The conversion of each of these sulfoxides to brefeldin A was monitored by observing the disappearance of the C-2 protons in the starting material and the appearance of the C-2 and C-3 alkene protons in brefeldin A. During this process, no other compounds beside these sulfoxides and brefeldin A were detected. The half-life for the conversion of the sulfoxide 13 to brefeldin A was 87.4 hours, while those of 15 and 20 were 4.81 and 1.87 hours, respectively. It is therefore clear that there is likely to be substantial conversion of the sulfoxides to regenerate brefeldin A during the in vitro cell culture cytotoxicity experiments, especially when one considers that the cull cultures are incubated at 37° C. and the present kinetics experiments were performed at 23° C. It is also evident that the sulfoxide 20 with the fastest rate of elimination contains a basic dimethylanino group which could facilitate the conversion through deprotonation of one of the C-2 protons α to the carbonyl.

To determine whether or not the conversion of brefeldin to various sulfide derivatives in fact has an appreciable effect on their solubilities, saturated solutions of brefeldin A and several of the derivatives were prepared in distilled water at room temperature and the concentrations were determined gravimetrically after evaporation of all of the water by azeotropic distillation with ethanol. The solubility of brefeldin A determined in this way was 2.8 mg/mL, while those of the sulfides were: 4, 10 mg/mL; 5, 12 mg/mL; 6, 40 mg/mL; and 11, 35 mg/mL. The increased solubilities of these derivatives will facilitate their formulations for biological evaluation.

The succinates and glutarates 22–25 ranged from being moderately cytotoxic to essentially inactive, and there was a difference in activity between the monoacylated and diacylated products. Of these four compounds, the monosuccinate 22 was the most active, displaying an MGM value of 2.5 $\mu$M. This was followed by the monoglutarate 23 (MGM 13 $\mu$M). The disuccinate 24 and diglutarate 25 were much less active, displaying MGMs of 89 $\mu$M and 98 $\mu$M, respectively.

The effect of sulfone vs. sulfoxide substitution can be seen by comparing the activities of 27 (MGM 3.5 $\mu$M) and 16 (MGM 0.68 $\mu$M). In this particular case, the sulfoxide is more cytotoxic. Oxidation of the C-10 to C-11 double bond in 27 to form 28 (MGM 31 $\mu$M) resulted in a significant loss of activity. This is consistent with the observation that epoxidation of the C-10 to C-11 double bond of brefeldin A results in a substantial loss of potency for induction of apoptotic DNA fragmentation.

Overall, the increase in biological activity seen with the conversion of the sulfides to the sulfoxides, along with the documented elimination of several of the sulfoxides to regenerate brefeldin A, provides strong support for the general strategy of employing the sulfide products formed from the addition of thiols to brefeldin A as prodrug candidates. Sulfides attached to acidic or basic functional groups appear to be particularly attractive, since these compounds can be converted to salts having increased solubility in an aqueous environment. Several of the more active brefeldin A derivatives are presently being evaluated in vivo in animal models as anticancer agents.

GENERAL EXPERIMENTAL METHODS $^1$H and $^{13}$C NMR spectra were recorded on a 300 MHz instrument. HMQC, $^1$H COSY, NOESY, and HMBC spectra were obtained on a 500 MHLz spectrometer. Merck silica gel 60-$F_{254}$ thin layer chromatography plates of 0.25 mm thickness were used and visualized with p-anisaldehyde stain. Flash chromatography was conducted using 60–200 mesh silica gel. (+)Brefeldin A was supplied by the National Cancer Institute. Unless otherwise indicated, all reagents were commercially available and used without further purification. Methylene chloride and dimethylformamide were stored over 4 Å molecular sieves prior to use. Tetrahydrofuran and diethyl ether were distilled from sodium/benzophenone ketyl radical. Microanalyses were performed at the Purdue Microanalysis Laboratory.

Example 1

2,3-Dihydro-(3R)-(2'methoxycarbonylethylthio)brefeldin A (2). Methyl mercaptopropionate (0.036, 0.3 mmol) was added to a solution of (+)-brefeldin A (0.056 g, 0.2 mmol) and PROTON SPONGES® (1,8-bis(dimethylamino) naphthalene sold under the trade name PROTON SPONGE® by Aldrich Chemical Co., 0.085 g, 0.4 mmol) in a mixture of MeOH (3 mnL) and water (1 mL) at room temperature. The reaction mixture was stirred at ambient temperature for 2 h, and then diluted with distilled water (10 mL). The aqueous solution was extracted with n-hexanes (3×15 mL) to remove PROTON SPONGE® and excess thiol. The resulting aqueous solution was then extracted with $CHCl_3$ (4×30 mL). The organic extracts were combined then dried over anhydrous $MgSO_4$ and the solvent was removed under a reduced pressure. The residue obtained was purified by means of flash column chromatography (silica gel, 1–3% $EtOH/CHCl_3$) to obtain the desired product 2 (0.075 g, 94%) as a oil. TLC Rf: 0.42 (10% $EtOH/CHCl_3$); $^1$H NMR ($CDCl_3$, 300 MHz) δ5.52 (m, 1H), 5.39 (m, 1H), 4.87 (m, 1H), 4.30 (m, 1H), 3.70 (s, 3H), 3.55 (dd, 1H, J=1.8 and 7.9 Hz), 3.42 (dt, 1H, J=2.2, 2.8 and 7.6 Hz), 2.90–2.72 (m, 2H), 2.68 (dd, 1H, J=3.3 and 16.6 Hz), 2.60 (m, 3H), 2.25 (dd, 1H, J=10.7 and 16.6 Hz), 2.15 (m,3H), 1.90 (m,3H), 1.65 (m, 3H), 1.60–1.30 (m,3H), 1.15 (d, 3H, J=6.1 Hz); $^{13}$C NMR ($CDCl_3$) δ172.40, 170.29, 135.54, 129.81, 76.57, 72.99, 71.65, 51.90, 45.76, 45.42, 44.39, 43.24, 40.72, 34.94, 34.85, 33.42, 31.27, 25.98, 25.10 and 20.32; IR ($CHCl_3$): 3439, 1725, 1629 and 1262 cm$^{-1}$; CIMS (m/z): 401 (MH$^+$); HRMS: Calcd for $C_{20}H_{32}O_6S$: 401.1998. Found: 401.1986.

Example 2

2,3-Dihydro-(3R)-(4'-hydroxyphenylthio)brefeldin A (3): 4-Hydroxyphenol (0.038 g, 0.3 mmol) was added to a solution of (+)-brefeldin A (0.056 g, 0.2 mmol) and PROTON SPONGE® (1,8-bis(dimethylaniino)naphthalene) (0.085 g, 0.4 mmol) in a mixture of MeOH (3 mL) and water (1 mL) at room temperature. The reaction mixture was stirred at ambient temperature for 12 h, and then diluted with distilled water (10 mL). The aqueous solution was extracted with n-hexanes (3×15 mL) to remove PROTON SPONGES® and excess thiol. The resulting aqueous solution was then extracted with $CHCl_3$ (4×30 mL). The organic extracts were combined and dried over anhydrous $MgSO_4$. The solvent was removed under a reduced pressure. The residue was purified by flash column chromatography (silica gel, 1% $EtOH/CHCl_3$) to obtain the desired product 3 (0.056 g, 70%) as an oil. TLC Rf: 0.28 (10% $EtOH/CHCl_3$); $^1$H NMR ($CDCl_3$, 300 MHz) δ7.38 (dd, 2H, J=2.1 and 8.7 Hz), 6.82 (dd, 2H, J=2.1 and 8.7 Hz), 5.47 (m, 1H), 5.34 (m, 1H), 4.94 (m, 1H), 4.23 (m, 1H), 3.70 (dd, 1H, J=3.2 and 10.9Hz), 3.49 (dt, 1H, J=1.38 and 10.8 Hz), 2.72 (dd, 1H, J=3.3 and 15 Hz), 2.37 (dd, 1H, J 10.8 and 15 Hz), 2.70–1.90 (m, 6H), 1.78–1.56 (m, 6H), 1.44 (br m, 1H) 1.30 (d, 3H, J 6.13 Hz); IR ($CHCl_3$): 3398, 1768, 1700, 1282 and 1042 cm$^{-1}$; HRMS: Calcd for $C_{22}H_{30}O_5S$: 406.1813. Found: 406.182 1.

Example 3

2,3-Dihydro-(3R)-(2'-N,N-dimethylaminoethylthiol) brefeldin A (4). N,N-Dimethylaminoethanethiol hydrochloride (0.105 g, 0.75 mmol) was added to a solution of (+)brefeldin A (0.140 g, 0.5 mmol) and PROTON SPONGE® (1,8-bis(dimethylamino)naphthalene) (0.214 g, 1.0 mmol) in a mixture of MeOH (9 mL) and water (3 mL) at room temperature. The reaction mixture was stirred at ambient temperature for 2 h, and then diluted with distilled water (30 mL). The aqueous solution was extracted with n-hexanes (3×30 mL) to remove PROTON SPONGE® and excess thiol. The resulting aqueous solution was then extracted with ethylacetate (4×60 mL). The organic extract was dried over anhydrous $MgSO_4$, and the solvent was removed under a reduced pressure. The residue obtained was purified by flash column chromatography (silica gel, 1–5% $EtOH/CHCl_3$) to obtain the desired product 4 (0.180 g, 94%) as an oil. TLC Rf: 0.2 (20% $MeOH/CHCl_3$); $^1H$ NMR ($CDCl_3$, 300 MHz) δ5.57 (m, 1H), 5.37 (dd, 1H, J=9, 15.3 Hz), 4.87 (m,1H), 4.31 (m, 1H), 3.67 (dd, 1H, J=1.8, 8.7 Hz), 3.49 (m, 1H), 2.60–2.76 (m, 5H), 2.41 (dd, 1H, J=10.5, 16.2 Hz), 2.32 (s, 6H), 2.08–2.26 (m, 3H), 1.97–2.06 (m, 3H), 1.68–1.82 (m, 3 H), 1.45–1.62 (m, 2H), 1.26 (d, 3H, J=6 Hz), 1.18 (m, 1H), $^{13}C$ NMR ($CDCl_3$) δ170.54, 135.55, 129.63, 72.86, 71.53, 60.29, 45.50, 45.37, 44.40, 43.13, 40.51, 34.94, 33.36, 31.31, 28.31, 25.06, 20.33; IR ($CHCl_3$): 3395, 1727, 1454, 1262, 1062 $cm_{-1}$; MS (m/z): 386 ($MH^+$); HRMS: Calcd for $C_{20}H_{35}O_4NS$: 386.2365. Found: 386.2376.

Example 4

2,3-Dihydro-(3R)-(2'-hydroxyethylthio)brefeldin A (5). 2-Mercaptoethanol (0.021 mL, 0.3 mmol) was added to a solution of (+)-brefeldin A (0.056 g, 0.2 mmol) and PROTON SPONGE® (1,8-bis(dimethylamino)naphthalene) (0.085 g, 0.4 mmol) in a mixture of methanol (3 mL) and water (13 mL) at room temperature. The reaction mixture was stirred at ambient temperature for 2 h, and then diluted with distilled water (10 mL). The aqueous solution was extracted with n-hexanes (3×15 mL) to remove PROTON SPONGE® and excess thiol. The resulting aqueous solution was saturated with NaCl and then extracted with ethylacetate (4×30 mL). The organic extracts were combined and dried over $MgSO_4$. The solvent was removed under reduced pressure. The residue obtained was purified by means of flash column chromatography (silica gel, 1–2% EtOH/ $CHCl_3$) to obtain the desired sulfide 5 (0.066 g, 93%) as an oil. TLC Rf: 0.29 (10% $EtOH/CHCl_3$); $^1H$ NMR ($CDCl_3$, 300 MHz) δ5.55(m, 1H), 5.39 (m, 1H), 4.90 (m, 1H), 4.32 (m, 1H), 3.78 (t, 2H, J=6.1 and 5.5 Hz and dd, 1H, for the C-4 proton are merged), 3.58 (t and dt, 3H), 2.90–2.65 (dd and m, 4H), 2.35 (dd, 1H, J=10.8 and 10.8 Hz), 2.22–1.90 (m, 6H), 1.85–1.40 (m, 3H), 1.22 (d, 3H, J=6.4 Hz); $^{13}C$ NMR ($CDCl_3$) δ170.70, 135.58, 129.72, 72,71, 72.15, 45.61, 44.42, 43.19, 40.58, 33.32, 31.25, 25.24, 20.32; IR ($CHCl_3$): 3398, 1768, 1700, 1282 and 1043 $cm^{-1}$; HRMS: Calcd for $C_{18}H_{30}O_5S$: 359.1892. Found: 359.1999.

Example 5

2,3-Dihydro-(3R)-(carboxymethyl)brefeldin A (6). Mercaptoacetic acid (0.042 mL, 0.6 mmol) was added to a solution of (+)-brefeldin A (0.140 g, 0.5 mmol) and PROTON SPONGES® (1,8-bis(dimethylamino)naphthalene) (0.214 g, 1.0 mmol) in a mixture of methanol (9 mL) and water (3 mL) at room temperature. The reaction mixture was stirred at ambient temperature for 48 h, and then diluted with distilled water (10 mL). The aqueous solution was extracted with n-hexanes (3×30 mL) to remove PROTON SPONGED® and excess mercaptoacetic acid. The resulting aqueous solution was diluted with MeOH (50 mL) and water:methanol was removed. The residue obtained was purified by flash column chromatography (silica gel, 5–20% $MeOH/CHCl_3$) to obtain the desired sulfide 6 (0.115 g, 62%) as an oil. TLC Rf: 0.32 (35% $MeOH/CHCl_3$); $^1H$ NMR ($D_2O$, 300 MHz) δ5.65 (m, 1H), 5.33 (m, 1H), 4.69 (m, 1H), 4.23 (m, 1H), 3.68 (bd, 1H, J=8.9 Hz), 3.42 (bd, 1H, J=9.8 Hz), 3.24 (bs, 1H), 2.65–2.85 (m, 3H), 2.46 (m, 1H), 1.50–2.40 (m 10H), 1.39 (m, 1H), 1.20(d, 3H, J=6.1 Hz); $^{13}C$ NMR ($D_2O$) δ180.48, 173.95, 135.01, 130.63,73.97, 71.96, 45.45, 44.02, 43.71, 42.26, 37.84, 34.89, 32.50, 30.77, 27.72, 24.66, 23.17, 19.38; IR ($CHCl_3$): 3469, 1701, 1282, 1128; MS (m/z): 373 ($MH^{3O}$); HRMS: Calcd for $C_{18}H_{28}O_6S$: 373.1685. Found: 373.1673.

Example 6

2,3-Dihydro-(3R)-(methoxycarbonylmethylthiol) brefeldin A (7). Methyl mercaptoacetate (0.025 g, 0.24 mmol) was added to a solution of (+)-brefeldin A (0.056 g, 0.2 mmol) and PROTON SPONGED® (1,8-bis (dimethylamino)naphthalene, 0.085 g, 0.4 mmol) in a mixture of MeOH (3 mL) and water (1 mL) at room temperature. The reaction mixture was stirred at ambient temperature for 2 h, and then diluted with distilled water (10 mL). The aqueous solution was extracted with n-hexanes (3×15 mL) to remove PROTON SPONGED® and excess thiol. The resulting aqueous solution was then extracted with ethylacetate or chloroform (4×30 mL). The organic extracts were combined and dried over $MgSO_4$. The solvent was removed under reduced pressure. The residue obtained was purified by flash column chromatography (silica gel, 1–3% EtOH/ $CHCl_3$) to obtain the desired product 7 (0.070 g, 91%) as an oil. TLC Rf: 0.57(10% $EtOH/CHCl_3$); $^1H$ NMR ($CDCl_3$, 300 MHZ) δ5.54 (m, 1H), 5.34 (, 1H), 4,.85 (m, 1H), 4.30 (m, 1H), 3.75 (s, 3H), 3.70 (dt, 1H, J=2.4 and 9.6 Hz), 3.67 (dd, 1H, J=1.6 and 8.3 Hz), 3.37 (d, 1H ,J=14.7 Hz), 3.26 (d, 1H, J=14.8 Hz), 2.75 (dd, 1H, J=3.2 and 16.7 Hz), 2.39 (dd, 1H, J=10.7 and 16.7 Hz), 2.28 (m, 1H), 2.15 (m, 2H), 2.05–1.45 (m, 9H), 1.20 (d, 3H, J=6.3 Hz); $^{13}C$ NMR ($CDCl_3$) δ171.25, 170.38, 135.45, 129.64, 72.58, 71.71, 52.51, 45.71, 45.60, 43.87, 43.06, 40.51, 34.57, 33.17, 32.33, 31.24, 24.99, 20.16; IR ($CHCl_3$): 3443, 1729 and 1280 $cm^{-1}$; CIMS (m/z): 387 ($MH^+$); HRMS: Calcd for $C_{18}H_{30}O_6S$: 387.1841. Found: 387.1832.

Example 7

2,3-Dihydro-(3R)-(2'-(Hydroxysulfonyl) ethylthiolbrefeldin A. Reaction of brefeldin A with 2-mercaptoethanesulfonic acid sodium salt gave 8 in 92% isolated yield as a solid; TLC Rf: o.125 (35% $EtOH/CHCl_3$); $^1H$ NMR ($D_2O$, 300 MHz) δ5.50 (m, 1H), 5.25 (m, 1H), peak for C-6 proton merged with $D_2O$ peak), 4.10 (m, 1H), 3.58 (bd, 1H, J=9.7 Hz), 3.28 (bd, 1H, 11.0 Hz), 3 10 (m, 2H), 2.80 (m, 2H), 2.68 (bd, 1H, J=15.11 Hz), 2.72–1.40 (m, 12H), 1.30 (m, 1H), 1.12 (d, 3H, J=6.17 Hz).

Example 8

2,3-Dihydro (3R)-(2',3'-dihydroxypropylthio) brefeldin A (8): 2,3-Dihydroxypropanethiol (0.063 mL, 0.75 mmol) was added to a solution of(+) brefeldin A (0.140 g, 0.5 mmol) and PROTON SPONGE (0.214 g, 1.0 mmol) in a mixture of methanol (9 mL) and water (3 mL) at room temperature. The reaction mixture was stirred at an ambient temperature for 2 h, and then diluted with distilled water (10 mL). The aqueous solution was extracted with n-hexanes (3×30 mL) to remove PROTON SPONGE and excess of thiol. The resulting aqueous solution was saturated with NaCl and then extracted with ethylacetate (4×60 mL). The organic extracts were combined and dried over $MgSO_4$. The solvent was removed under. reduced pressure. The residue obtained was purified by flash column chromatography (silica gel, 1–10% $EtOH/CHCl_3$) to obtain the desired sulfide 9 (0.150 g, 79%) as an oil. TLC Rf: 0.5 (20% $EtOH/CHCl_3$); $^1H$ NMR (300 MHz, $CD_3OD$) δ5.54 (m, 1H), 5.29 (m, 1H), 4.71 (m, 1H), 4.11 (m, 1H), 3.58–3.75 (m, 1H), 3.48–3.55 (m, 2H), 3.52 (m, 2H), 3.42 (b d, 1H, J=10.4 Hz), 2.50–2.80 (m, 3H), 2.10–2.30 (m,2H) 1.45–2.10 (m, 10H), 1.35 (d, 3H, J=5.8 Hz); $^{13}$C NMR (CD$_3$OD): δ172.92, 136.92, 130.72, 73.46, 73.20, 72.83, 65.89, 65.64, 47.38, 47.32, 46.74, 46.33, 45.38; IR (CHCl$_3$) 3401, 1765, 1705, 1280, 1041 cm$^{-1}$; MS (m/z): 389 (MH$^{3O}$); HRMS: Calcd for C$_{19}$H$_{32}$O$_6$S: 389.1998. Found: 389.2006.

Example 9

2,3-Dihydro-(3R)-(2')-aminoethylthio)brefeldin A (9): 2-Aminoethanethiol hydrochloride (0.085 mL, 0.75 mmol) was added to a solution of (+) brefeldin A (0.140 g, 0.5 mmol) and PROTON SPONGE (0.214 g, 1.0 mmol) in a mixture of methanol (9 mL) and water (3 mL) at room temperature. The reaction mixture was stirred at an ambient temperature for 2 h, and then diluted with distilled water (10 mL). The aqueous solution was extracted with n-hexanes (3×30 mL) to remove PROTON SPONGE and excess of thiol. The resulting aqueous solution was diluted with methanol (50 mL) and the water:methanol azeotrope removed. The residue obtained was purified by means of flash column chromatography (silica gel, 5–20% MeOH/CHCl$_3$) to obtain 0.170 g (95%) of the desired sulfide 10. TLC Rf: 0.13 (50% EtOH/CHCl$_3$); $^1$H NMR (300 MHz, CD$_3$OD) δ5.56 (m, 1H), 5.29 (m, 1H), 4.76 (m, 1H), 4.17 (m, 1H), 3.70 (bd, 1H), 3.30 (bd, 1H), 3.22 (m, 2H), 3.10–3.00 (m, 2H), 2.90–2.75 (m, 2H), 2.64 (dd, 1H, J=3.8 and 16.2 Hz), 2.40 (m, 1H), 2.20–1.84 (m, 5H), 1.80–1.45 (m, 6H), 1.36 (m, 1H), 1.21 (m and d, 4H, J=6.3 HZ); $^{13}$C NMR (CD$_3$OD) δ172.39, 136.90, 130.88, 73.47, 73.13, 47.45, 46.69, 46.46, 45.52, 43.99, 41.01, 40.11, 36.20, 34.13, 32.46, 29.65, 26.45, 20.54; IR (CHCl$_3$): 3377, 1704, 1629, 1508, 1458, 1267 cm$^{31\ 1}$; MS (m/z): 358 (MH); HRMS: Calcd for C$_{18}$H$_{31}$NO$_4$S: 358.2052. Found: 358.2059.

Example 10

2,3-Dihydro-(3R)-(4'-methoxyphenylthio)brefeldin A (10). Mercaptoanisole (0.092 mL, 0.75 mmol) was added to a solution of (+) brefeldin A (0.140 g, 0.5 mmol) and PROTON SPONGE (0.214 g, 1.0 mmol) in a mixture of methanol (9 mL) and water (3 mL) at room temperature. The reaction mixture was stirred at an ambient temperature for 12 h, and then diluted with distilled water (20 mL). The aqueous solution was extracted with n-hexanes (3×30 mL) to remove PROTON SPONGE and excess thiol. The resulting aqueous solution was saturated with NaCl and then extracted with chloroform (4×60 mL). The organic extracts were combined and dried over MgSO$_4$. The solvent was removed under reduced pressure. The residue obtained was purified by flash column chromatography (silica gel, 1–3% EtOH/CHCl$_3$) to yield the desired sulfide 11 (0.056 g, 67%) as an oil. TLC Rf: 0.62 (10% EtOH/CHCl$_3$,); $^1$H NMR (CDCl$_3$, 300 MHz) δ7.43 (dd, 2H, J=2.8 and 8.7 Hz), 6.87 (dd, 2H, J=2.7 and 8.7 Hz), 5.45 (m, 1H), 5.35 (m, 1H), 4.92 (m, 1H), 4.29 (m, 1H), 3.82 (s, 3H), 3.76 (dt, 1H, J=1.7 and 10.2 Hz), 3.45 (dd, 1H, J=1.6 and 8.5 Hz), 2.75 (dd, 1H, J=3.1 and 16.5 Hz), 2.35 (dd, 1H, J=10.8 and 16.5 Hz), 2.20–1.85 (m, 5H), 1.80–1.35 (m, 7H), 1.25 (d, 3H, J=6.28 Hz); $^{13}$C NMR (CDCl$_3$) δ170.50, 159.77, 137.06, 135.60, 135.35, 129.52, 124.16, 114.92, 114.76, 76.59, 72.80, 71.56, 55.32, 50.96, 45.22, 44.11, 43.03, 40.77, 34.13, 33.42, 31.26, 24.96, and 20.42; IR (CHCl$_3$): 3433, 1716, 1593 and 1488 cm$^{-1}$; MS (m/z): 420 (W); HRMS: Calcd for C$_{23}$H$_{32}$O$_5$S: 420.1970. found: 420.1965.

Example 11

2,3-Dihydro-(3R)-(S-L-cysteinyl)brefeldin A (11). (R)-(L)-Cysteine (0.816 g, 6.75 mmol) was added to a solution of (+) brefeldin A (2.1 g, 7.5 mmol) and PROTON SPONGE (3.21 g, 15 mmol) in a mixture of Methanol (80 mL) and water (40 mL) at room temperature. The reaction mixture was stirred at an ambient temperature for 5 h and diluted with methanol (200 mL). The methanolic solution was concentrated. To the resulting residue was added chloroform (200 3 mL), the mixture stirred for 5 minutes, filtered and washed with chloroform (2×50 mL) to obtain the requisite sulfide 12 (1.8 g 65%). mp 178° C.; TLC Rf. 0.25 (30% MeOH/CHCl$_3$); $^1$H NMR (D$_2$O, 300 MHz) δ7.6 (bm, 2H), 5.60 (m, 1H), 5.22 (m, 1H), 4.70 (m, 1H), 4.14 (m, 1H), 3.7 6 (m, 1H), 3.66 (bd, 1H, J=7.3 Hz), 3.44 (bd, 1H, J=8.6 Hz), 3.09 (m, 2H), 2.70 (bd, 1H, J 16.4 Hz), 2.40–2.10 (m, 2H), 2.10–1.80 (m, 4H), 1.75–1.50 (m, 5H), 1.29 (m, 1H), 1.13 (d, 3H, J=6.3 Hz); $^{13}$C NMR (D$_2$O) δ174.46, 172.94, 135.70, 131.95, 74.98, 72.83, 55.05, 46.61, 46.34, 44.49, 42.94, 39.18, 36.28, 33.36, 33.30, 31.49. 25.66, 20.27; MS (m/z): 402 (MH$^+$); HRMS: Calcd for C$_{19}$H$_{31}$O$_6$NS: 402.1950. Found: 402.1951.

Example 12

2,3-Dihydro-(3R)-(glutathionyl)brefeldin A (12): Glutathione (0.138 g, 0.4 mmol) was added to a solution of (+) brefeldin A (0.140 g, 0.5 mmol) and PROTON SPONGE (0.214 g, 1.0 mmol) in a mixture of methanol (2 mL) and water (2 mL) at room temperature. The reaction mixture was stirred at an ambient temperature for 5 h and diluted with methanol (40 mL), After the methanolic solution was concentrated, chloroform (75 mL) was added. The mixture was stirred for 5 minutes, filtered and then washed with chloroform (2×25 mL) to obtain the requisite sulfide 13 (0.130 g, 44%). TLC Rf: 0.13 (40% MeOH/CHCl$_3$); $^1$H NMR (CD$_3$OD+D$_2$O, 300 MHz) δ5.56 (m, 1H), 5.19 (m, 1H), 4.69 (m, 1H, partially merged with solvent peak), 4.45 (m, 4H), 4.06 (m, 1H), 3.70–3.45 (m, 3H), 3.40–3.10 (m, 3H) 2.80–2.50 (m, 2H), 2.40 (m, 1H), 2.40–2.00 (m, 2H), 1. 80 (m, 2H), 1.80–1.50 (m, 4H), 1.20 (m, 1H), 1.10 (d,3H, J 6.4 Hz), 1.05 (m, 1H); HRMS Calcd for C$_{26}$H$_{41}$O$_{10}$N$_3$S: 610.2410. Found: 610.2435.

Example 13

2,3-Dihydro-(3R)-(2'-methoxycarbonylethylsulfinyl) brefeldin A (13). To a solution of sulfide 2 (0.180 g, 0.45 mmol) in methylene chloride (45 ML) was added m-CPBA (85% Aldrich, 0.100 g, 0.5 mmol) in a one portion at 0° C. under N$_2$ atmosphere. TLC analysis of the reaction mixture showed that the reaction was completed within 3 minutes. The reaction mixture was then neutralized with saturated aqueous solution of NaHCO$_3$ (5 mL) and extracted with ethylacetate (3×75 mL). The organic extracts were combined and dried over MgSO$_4$. The solvent was removed under reduced pressure. The resulting residue was purified by flash column chromatography (silica gel, 2% EtOH/CHCl$_3$) to afford the desired sulfoxide 14 (0.150 g 80%) as an oil. TLC Rf: 0.35 (10% EtOH/CHCl$_3$); $^1$H NMR (CDCl$_3$, 300 MHz) δ5.40 (m, 2H), 4.94 (m, 1H), 4.32 (m, 1H), 4.18 (br d, 1H, J 10.16 Hz), 3.74 (s, 3H), 3.44 (dd, 1H, J=3.1 and 8.5 Hz), 3.09 (br t, 3H), 2.95 (dd, 1H. J=3.4 and 17.8 Hz), 2.88 (t, 1H, J=7.1 Hz), 2.80 (br d, 1H, J=8.8 Hz), 2.66 (dd, 1H, J=8.3 and 8.3 Hz), 2.30–1.80 (m, 6H), 1.80–1.40 (m, 5H), 1.25 (m, 1H), 1.17 (d, 3H, J=6.3 Hz); $^{13}$C NMR (CDCl$_3$) δ171.41, 169.42, 136.25, 129.71, 75.88, 72.97, 72.52, 71.87; 52.27, 45.49, 44.52, 43.21, 40.70, 33.45, 30.33, 29.87, 27.42, 24.54, 20.29; IR (CHCl$_3$): 3387, 1725, 1649, 1439, 1358, 1263 cm$^{-1}$; MS (m/z): 417 (MH$^+$); HRMS:: Calcd for C$_{20}$H$_{32}$O$_7$S: 417.1947. Found: 417.1955.

Example 14

2,3-Dihydro-(3R)-(4'-hydroxyphenylsulfinyl)brefeldin A (14): To a solution of sulfide 3 (0.050 g, 0.123 mmol) in methylene chloride was added m-CPBA (85% Aldrich, 0.028 g, 0.135 mmol) in a one portion at 0° C. under N$_2$ atmosphere. Analysis of the reaction mixture by TLC indicated that the reaction was completed within 3 minutes. The reaction mixture was then neutralized with saturated aqueous solution of NaHCO$_3$ (5 mL) and extracted with ethylacetate (3×50 mL). The organic extracts were combined and dried over MgSO$_4$. The solvent was removed under reduced pressure. The resulting residue was purified by flash column chromatography (silica gel, 2% EtOH/CHCl$_3$) to afford the desired sulfoxide 15 (0.035 g 68%) as an oil. TLC Rf: 0.18 (10% EtOH/CHCl$_3$); $^1$H NMR (CDCl$_3$+CD$_3$OD, 300 MHz) δ7.43 (d, 2H, J=8.8 Hz), 6.95 (d, 2H, J=8.6 Hz), 5.23 (m, 2H), 4.78 (m, 1H), 4.04 (m, 1H), 3.78 (br d, 1H, J=10.2 Hz); 3.32 (dd, 1H, J=3.3 and 8.3 Hz), 2.82 (dd, 1H, J=3.5 and 17.6), 2.63 (dd, 1H, J=17.6 and 17.6 Hz), 2.10–1.70 (m, 5H), 1.70–1.30 (m, 6H), 1.25 (m, 1H), 1.03 (d, 3H, J=6.2 Hz).

Example 15

2,3-Dihydro-(3R)-(2'-hydroxyethylsulfinyl)brefeldin A (15). To a solution of dialkyl sulfide 5 (0.072 g, 0.2 mmol) in a mixture of tetrahydrofuran (2.5 mL) and methylene chloride (2.5 mL) was added m-CPBA (85% from Aldrich, 0.049 g, 0.24 mmol) in one portion at 0° C. under N$_2$ atmosphere. Analysis of the reaction mixture by TLC indicated that the reaction was completed within 2 minutes. The reaction mixture was neutralized with aqueous saturated NaHCO$_3$ solution (5 mL). The aqueous layer was separated, diluted with ethanol (20 mL), and filtered to remove the precipitated salts. The filtrate was concentrated, and the resulting residue was flash chromatographed (silica gel, CHCl$_3$-5% EtOH/CHCl$_3$) to afford the desired product 16 (0.046 g, 62%) as an oil. TLC Rf: 0.44 (15% EtOH/CHCl$_3$); $^1$H NMR (CDCl$_3$, 300 MHz) δ5.40 (m, 2H), 4.96 (m, 1H), 4.30 (m, 1H), 4.14 (m, 3H), 3.54 (dd, 1H, J=3.6 and 7.9 Hz), 3.02 (m, 2H), 2.93 (dd, 1H, J=3.7 and 17.3 Hz), 2.66 (dd, 1H, J 16.4 and 17.4 Hz), 2.15–1.88 (m, 6H), 1.80–1.45 (m, 5H), 1.25 (m, 1H), 1.19 (d, 3H, J 6.3 Hz); $^{13}$C NMR (CDCl$_3$) δ169.94, 135.66, 129.95, 77.19, 71.87, 71.70, 58.28, 55.85, 51.81, 45.23, 44.15, 43.21, 40.17, 33.46, 33.46, 30. 13, 29.00, 23.86, 20.19; IR (CHCl$_3$): 3377, 1720, 1443, 1263, 1058, 987 cm$^{-1}$; MS (m/z): 375 (MH$^+$); HRMS: Calcd for C$_{18}$H$_{30}$O$_6$S: 375.1841. Found: 375.1856. Found: 375.1856.

Example 16

2,3-Dihydro-(3R)-(2'-methoxycarbonylmethylsulfinyl) brefeldin A (16). To a solution of sulfide 7 (0.145 g, 0.38 mmol) in methylene chloride (8 mL) was added m-CPBA (85% Aldrich, 0.084 g, 0.41 mmol) in a one portion at 0° C. under N$_2$ atmosphere. Analysis of the reaction mixture by TLC indicated that the reaction was completed within 3 minutes. The reaction mixture was then neutralized with a saturated aqueous solution of NaHCO$_3$ (5 mL) and then extracted with ethylacetate (3×75 mL). The organic extracts were combined and dried over MgSO$_4$. The solvent was removed under reduced pressure. The resulting residue was purified by flash column chromatography (silica gel, 2% CHCl$_3$) to afford the desired sulfoxide 17 (0.125 g, 83%) as an oil. TLC Rf: 0.34 (10% EtOH/CHCl$_3$); $^1$H NMR (CDCl$_3$, 300 MHz) δ5.56–5.30 (m, 2H), 4.94 (m, 1H), 4.31 (m, 1H), 4.12 (dt, 1H, J=3.7 and 9.8 Hz), 3.95 (d, 1H, J=13.9 Hz), 3.82 (s, 3H), 3.77 (d, 1H, J=13.8 Hz), 3.69 (dd, 1H, J=3.6 and 7.9 Hz), 2.95 (dd, 1H, J=3.9 and 17.4 Hz), 2.70 (dd, 1H, J=8 and 17.5 Hz), 2.35–1.82 (m, 7H), 1.80–1.40 (m, 4H), 1.25 (m, 1H), 1.19 (d, 3H, J=6.3 Hz); $^{13}$C NMR (CDCl$_3$) δ169.48, 165.40, 135.98, 129.98, 72.65, 72.31, 71.87, 56.78, 53.36, 53.05, 45.69, 44.03, 43.19, 40.61, 33.33, 30.25, 29.22, 24.27, 20.20; IR (CHCl$_3$): 3377, 1740, 1725, 1704, 1639, 1433, 135 8, 1263 cm$^{-1}$; MS (m/z): 403 (MH$^+$); HRMS: Calcd for C$_{19}$H$_{30}$O$_7$S: 403.1791. Found: 403.1787.

Example 17

2,3-Dihydro-(3R)-(2 9 3'-dihydroxypropylsulfinyl) brefeldin A (17). To a tetrahydrofuran:methylene chloride (1:1 v/v; 8 mL) solution of dialkyl sulfide 9 (0.057 g, 0.15 mmol) was added m-CPBA (85% from Aldrich, 0.032 g, 0.16 mmol) in one portion at 0° C. under N$_2$ atmosphere. Analysis by TLC indicated that the reaction was completed within 2 minutes. The reaction mixture was neutralized with aqueous saturated NaHCO$_3$ solution (5 mL). The aqueous layer was separated, diluted with ethanol (20 mL) and filtered to remove precipitated salts. The filtrate was concentrated and the resulting residue was purified by flash chromatography (silica gel, 5% EtOH/CHCl$_3$) to afford 0.030 g (50%) of the desired product 18 as a colorless oil. TLC Rf: 0.27 (20% EtOH/CHCl$_3$).

Example 18

2,3-Dihydro-(3R)-(2'-aminoethylsulfinyl)brefeldin A (18). To a tetrahydrofuran:methylene chloride (1:1) solution of dialkyl sulfide 10 (0.080 g, 0.22 mmol) was added m-CPBA (85% from Aldrich, 0.050 g, 0.25 mmol) in one portion at 0° C. under N$_2$ atmosphere. Analysis by TLC indicated that the reaction was completed within 3 minutes. The reaction mixture was neutralized with aqueous saturated NaHCO$_3$ solution (5 mL). The aqueous layer was separated, diluted with EtOH (20 mL) and the precipitated salt was removed by filtration. The filtrate was concentrated, and the resulting residue was purified by flash chromatography (silica gel, 50% EtOH/CHCl$_3$) to afford the desired product 19 (0.055 g, 66%) as a colorless oil. TLC Rf: 0.1 (80% EtOH/CHCl$_3$); $^1$H NMR (CD$_3$OD, 300 MHz) δ7.24 (m, 1H), 5.54–5.10 (m, 2H), 4.85 (m, 1H, merged with solvent peak), 4.09 (m, 1H), 3.84 (br d, 1H, J=10.3 Hz), 3.50 (dd, 1H, merged with ethanol peak), 3.37 (m, 2H), 3.19 (m, 2H), 2.85 (dd, 1H, J=3.5 and 15.6 Hz), 2.58 (dd, 1H. J=15.0 and 17.0 Hz), 2.35–1.25 (m, 12H), 1.13 (d, 3H, J=6.3 Hz).

Example 19

2,3-Dihydro-(3R)-(4 methoxyphenylsulfinyl)brefeldin A (19). To a cold (0° C.) methylene chloride (10 mL) solution of sulfide 11 (0.100 g, 0.24 mmol) was added m-CPBA (85% Aldrich, 0.053 g, 0.26 mmol) in a one portion, under N$_2$ atmosphere. Analysis of the reaction mixture by TLC indicated that the reaction was completed within 3 minutes. The reaction mixture was then neutralized with saturated aqueous solution of NaHCO$_3$ (5 mL) and extracted with ethylacetate (3×75 mL). The organic extracts were combined and dried over MgSO$_4$. The solvent was removed under reduced pressure. The resulting residue was purified by flash column chromatography (silica gel, 5%EtOH/CHCl$_3$) to afford the desired sulfoxide 20 (0.090 g, 87%) as an oil. TLC Rf: 0.45 (10% EtOH/CHCl$_3$); $^1$H NMR (CDCl$_3$, 300 MHz) δ7.55 (d, 2H, J=8.4 Hz), 7.13 (d, 2H, 7.9 Hz), 5.40–5.20 (m, 2H), 5.02 (m, 1H), 4.15 (m, 1H), 3.90 (s, 3H), 3.84 (br d, 1H, J=10.9

Hz), 3.50–2.95 (m, 2H), 2.20–1.35 (m, 12H), 1.28 (d, 3H, J=6.2 Hz); MS (m/z): 437 (MH$^+$); HRMS: Calcd for C$_{23}$H$_{32}$O$_6$S: 437.1998. Found: 437.2007.

Example 20

2,3-Dihydro-(3R)-[21-N,N-(dimethylamino) ethylsulfinyl]brefeldin A (20). Solid m-CPBA (85% from Aldrich, 0.22 g, 1.2 mmol) was added in one portion at to a tetrahydrofuran:methylene chloride (1:1 v/v; 40 mL) solution of sulfide 4 (0.35 g, 0.92 mmol) at 0° C. under N$_2$ atmosphere. Analysis of the reaction mixture by TLC indicated that the reaction was completed within 3 min. The reaction mixture was neutralized with aqueous saturated NaHCO$_3$ solution (10 mL). The aqueous layer was separated then diluted with ethanol (80 mL). The precipitated salt removed by filtration. The filtrate was concentrated and the resulting residue was purified by flash chromatography (silica gel, CHCl$_3$-5% MeOH/CHCl$_3$) to afford 0.27 g (75%) of the desired product 21. TLC Rf: 0.54 (30% MeOH/CHCl$_3$); $^1$H NMR (CDCl$_3$, 300 MHz) δ5.38 (m, 2H), 4.97 (m, 1H), 4.25 (m, 1H), 4.13 (br d, 1H, J=10.1 Hz), 3.38 (dd, 1H, J=5.8 and 7.1 Hz), 3.02–2.60 (m, 5H), 2.28 (s, 6H), 2.27–1.85 (m, 4H) 1.76–1.38 (m, 6H), 1.20 (m, 1H), 1.14 (d, 3H, J=6.4 Hz). FAB Mass: 402 (MH$^+$).

Example 21

2,3-Dihydro-(3R)-(S-L-cysteinyl)brefeldin A Sulfoxide (21). A HCl dioxane solution (4M, 2.24 ml, 8.96 mmol) was added over a period of 5 min to an anhydrous tetrahydrofuran (50 mL) solution of sulfide 12 (1.8 g, 4.48 mmol) at 0° C. under N$_2$ atmosphere. The reaction mixture was maintained at 0° C. for 24 h, then treated with m-CPBA (85%, Aldrich, 1.06 g, 5.38 mmol), and stirred for an additional 10 minutes at 0° C. The resulting sulfoxide precipitated from solution. The precipitated sulfoxide was collected by cold filtration of the reaction solution and washed with cold tetrahydrofuran (2×50 mL) to yield 1.69 (86%) of the desired sulfoxide 22: mp 120° C. TLC (Whatman 250 μm silica gel glass plates) Rf: 0.22 (30% MeOH/CHCl$_3$); $^1$H NMR (CD$_3$OD, 300 MHz) δ5.54 (m, 1H), 5.42 (mn, 1H), 4.95 (m, 1H), 4.56 (m, 1H), 4.22 (m, 1H), 3.97 (bd, 1H), J=9.9 Hz), 3.76 (m, 1H), 3.48 (m, 2H), 2.96–2.75 (m, 1H), 2.38–1.85 (m, 7H), 1.80 –1.40 (m, 5H), 125 (d, 3H, J=6.4 Hz); MS (m/z): 418 (MH$^+$).

Example 22

Brefeldin A 8 0-Succinate (22). Brefeldin A (0.056 g, 0.2 mmol) was dissolved in pyridine (4 mL) and succinic anhydride (0.025 g, 0.25 mmol) was added. The reaction mixture was stirred at 60° C. for 48 h. The reaction mixture was then diluted with water (40 mL), and the mixture was extracted with chloroform (3×25 mL). The combined organic layers were washed in succession with 1 N aqueous HCl solution (2×25 mL) and brine. The organic lay was dried over (MgSO$_4$) and then filtered. The solvent was removed under reduced pressure to afford an oil that was purified by flash chromatography (silica gel CHCl$_3$-5% Methanol in CHCl$_3$). The succinate was collected and recrystallized from a diethyl ether:hexanes to afford the succinate ester 23 (0.035 g, 46%) as a white solid: TLC Rf 0.66 (CHCl$_3$/MeOH, 4:1, silica gel); $^1$H NMR (CDCl$_3$, 300 MHz) δ7.35 (dd, 1H, J=3, 15.6 Hz), 5.92 (dd, 1H, J=1.8, 15.6 Hz), 5.72 (m, 1H), 5.17–5.33 (overlapping m and dd, 2H, J 9, 15.3 Hz), 4.87 (m, 1H), 4.12 (ddd, 1H, J=2.1, 2.4, 9 Hz), 2.63 (m, 5H), 2.20–2.42 (m, 2 H), 2.02 (br m, 1H), 1.68–1.91 (m, 5H), 1.48–1.63 (m, 2H), 1.26 (d, 3H, J=6.3 Hz), 0.89–1.0 (br m, 1H); low resolution FABMS m/z (relative intensity) 403 (M+Na+, 5), 381 (MH$^+$, 20), 363 (MH$^+$-18, 15); high resolution FABMS calcd. MH$^+$381.1913, found 381.1900.

Example 23

Brefeldin A 8 0-Glutarate (23). Brefeldin A (0.056 g, 0.2 mmol) was dissolved in pyridine (4 mL) and glutaric anhydride (0.04 g, 0.35 mmol) was added. The reaction mixture was heated to 110° C. under argon for 36 h. Analysis of the reaction mixture by TLC (CHCl$_3$/Methanol, 4:1, silica gel) indicated the presence of a major spot with an Rf of 0.58 and a very minor spot at Rf 0.19 along with a spot corresponding to unreacted starting material. The reaction mixture was cooled to room temperature and diluted with water (40 mL). Purification and isolation as reported above for the synthesis of 23 afforded the desired monoglutarate derivative 24 (0.033 g, 42%) as a white solid: TLC Rf 0.58 (CHCl$_3$/MeOH, 4:1, silica gel); low resolution FABMS m/z 417 (M+Na$^+$), 395 (MH$^+$), 377 (MH$^+$-18).

Example 24

Brefeldin A Disuccinate (24). In a manner similar to that reported below for the synthesis of 26, the reaction of brefeldin A (0.056 g, 0.2 mmol) and succinic anhydride afforded the desired diester 25 (0.051 g, 53%) as an off-white solid: TLC Rf 0.24 (CHCl$_3$/MeOH, 4:1, silica gel); $^1$H NMR (CDCl$_3$, 300 MHz) δ7.19 (dd, 1H, J=3.6, 15.6 Hz), 5.70 (m, 2H), 5.33 (br m, 2H), 5.19 (dd, 1H, J=9, 15 Hz), 4.90 (m, 1H), 2.85–2.93 (m, 1H), 2.54–2.74 (m, 8H), 2.32–2.47 (m, 2H), 1.94–2.05 (m, 3H), 1.69–1.89 (m, 3H), 1.47–1.64 (m, 2H), 1.25 (d, 3H. J=6 Hz), 0.96–1.04 (m, 1H); low resolution FABMS m/z 503 (M+Na$^+$), 481 (MH$^+$); high resolution FABMS calcd. MH$^+$481.2074, found 481.2084.

Example 25

Brefeldin A Diglutarate (25). Brefeldin A (0.056 g, 0.2 mmol) was dissolved in pyridine (4 mL) and glutaric anhydride (0.07 g, 0.6 mmol) was added to this solution followed by DMAP® (dimethylamino pyridine) (0.05 g, 0.4 mmol). The reaction mixture was heated to 60° C. and maintained for a period of 48 h under argon. Analysis of the reaction mixture by TLC (CHCl$_3$/MeOH, 4:1, silica gel) indicated the formation of a major product characterized with an Rf of 0.19. The reaction mixture was cooled, diluted with water and the pH of the solution was adjusted to 4, The solution was extracted with chloroform (3×25 mL). The chloroform extracts were combined and washed with 1 N HCl (2×30 mL), brine (50 mL), then dried over MgSO$_4$ and filtered. The solvent was removed under reduced pressure. The residue was purified by flash chromatography (silica gel 1%–6% MeOH:CHCl$_3$). The fractions containing the product were pooled and evaporated to afford a gum. This material was recrystallized from a mixture of ethyl acetate and hexanes to afford the diester 26 (0.041 g, 40%) as a white solid: TLC Rf 0.19 (CHCl$_3$/MeOH, 4:1, silica gel); $^1$H NMR (CDCl$_3$, 300 MHz) δ7.23 (dd, 1H, J=3.6, 15.9 Hz), 5.68–5.77 (overlapping m and d, 2H, J=1.8, 15.9 Hz), 5.28 (m, 1H), 5.21 (dd, 1H, J=9.3, 15.3 Hz), 5.15 (m, 1H), 2.25–2.55 (overlapping m and t, 11H, J=7.2 Hz), 1.93–2.10 (overlapping m and t, 8H, J=7.2 Hz), 1.79–1.91 (m, 1H), 1.65–1.74 (m, 1H), 1.50–1.63 (m, 2H), 125 (d, 3H, J=6.3 Hz), 0.86–0.99 (br m, 1H); low resolution FABMS m/z 531 (M$^+$+Na), 509 (MH+); high resolution FABMS calcd. MH$^+$509.2387, found 509.2397.

Example 26

2,3-Dihydro-2,3-dihydroxybrefeldin A (26): To a solution of (+)-brefeldin A (0.056 g, 0.2 mmol) in tert-butanol:water (2:1 v/v; 6 mL) at room temperature was added NMO (4-methyl morpholine N-oxide) (0.047 g, 0.4 mmol) followed by OsO$_4$ (1 wt % solution in H$_2$O, 4 drops). The reaction progress was monitored by TLC. The reaction mixture was stirred at room temperature for 4 h, quenched with brine (5 mL), extracted with ethyl acetate (3×40 mL). The ethyl acetate extracts were combined and dried over anhydrous MgSO$_4$. The solvent was removed under reduced pressure. The resulting residue was crystallized from methanol:ethylacetate:hexanes (1:1:3, v/v) solvent system to afford the product 27 (0.056 g, 89%); m.p. 183° C.; $^1$H NMR (CDCl$_3$ +CD$_3$OD, 300 MHz) δ5.40–5.22 (m, 2H), 4.80 (m, 1H), 4.08 (m, 1H), 3.58 (m, 1H), 3.28 (mn, 1H), 2.82 (m, 1H), 2.60 (m, 2H), 2.45–2.20 (m, 3H), 2.10–1.80 (m, 6H), 1.60–1.20 (m, 4H), 1.20 (d. 3H, J=6.2 Hz); IR(MeOH): 3317, 1730, 1438, 1237, 1132, 1102 cm$^-$; MS (m/z): 315 (MH$^+$); HRMS: Calcd for C$_{16}$H$_{26}$O$_6$:315.1808. Found: 315.1814.

Example 27

2,3-Dihydro(3R)-(methoxycarbonylmethylsulfonyl) brefeldin A (27). To a dry reaction flask equipped with a rubber septum and a magnetic stirring bar was placed sulfide 7 (0.087 g, 0.2 mmol) and methylene chloride (10 mL) at room temperature under N$_2$. The reaction solution was cooled to 0° C. and m-CPBA (85% from Aldrich, 0.091 g, 0.44 mmol) was added in one portion. The reaction mixture was stirred for an additional 4 h., quenched with saturated aqueous NaHCO$_3$ solution (10 mL), stirred for an additional 20 min. and extracted with chloroform (3×40 mL). The organic extracts were combined, dried over anhydrous MgSO$_4$, and filtered. The solvent was removed under reduced pressure. The resulting residue was purified by flash column chromatography (CHCl$_3$-2% EtOH/CHCl$_3$) to yield the desired sulfone 28 (0.032 g, 40%) as an oil. TLC Rf: 0.53 (10% EtOH/CHCl$_3$); $^1$H NMR (CDCl$_3$, 300 Mz) δ5.66 (m, 1H), 5.44 (m, 1H), 4.90 (m, 1H), 4.46 (dd, 1H, J=2.9 and 9.5 Hz), 4.36 (m, 1H), 4.22 (d, 1H, J=14.4 Hz), 4.08 (d, I H, J=14.4 Hz), 4.08 (m, 1H), 3.88 (s, 3H), 3.13 (bs, 1H), 2.96 (dd, 1H, J=17.6 and 17.7 Hz), 2.84 (dd, 1H, J 3.0 and 17.7 Hz), 2.36 (m, 1H), 2.30–1.95 (m, 5H), 1.85–1.45 (m, 7H), 1.22 (d, 3H, J=6.3 Hz); $^{13}$C NMR (CDCl$_3$) δ168.741, 163.382, 135.774, 129.604, 77.217, 73.759, 72.774, 72.428, 62.128, 56.501, 53.421, 46.115, 43.213, 40.948, 33.048, 31.118, 28.261, 24.804, 19.984; IR (CHCl$_3$): 3518, 3387, 1735, 1438, 1318, 1278, 1147, 1112 cm$^{-1}$; MS (m/z): 419 (M$^+$); HRMS: Calcd for C19H$_{30}$O$_8$S: 419.1740. Found: 419.1757.

Example 28

2,3-Dihydro-10,11-epoxy-(3R)-(21-methoxycarbonylmethylsulfonyl)-brefeldin A (28). To a dry reaction flask equipped with a rubber septum and a magnetic stirring bar was placed sulfide 7 (0.064 g, 0.165 mmol) and methylene chloride (10 mL) at room temperature under N$_2$. The reaction solution was cooled to 0° C. and m-CPBA (85% from Aldrich, 0.150 g, 0.72 mmol) was added in one portion. The reaction mixture was stirred for 7 h, then quenched with a saturated aqueous NaHCO$_3$ solution (10 mL). The reaction mixture was extracted with methylene chloride (3×30 mL). The organic extract were combined over dried anhydrous MgSO$_4$, and filtered. The solvent was removed. The resulting residue was purified by silica gel flash column chromatography (CHCl$_3$-2% EtOH/CHCl$_3$) to yield the desired epoxysulfone 29 (0.035 g, 50%).m.p. 180° C. TLC Rf: 0.53 (10% EtOH/CHCl$_3$); $^1$H NMR (CDCl$_3$, 300 MHz) δ5.25 (m, 1H), 4.35–4.28 (m, 2H), 4.10 (d, 1H, J=14.6 Hz), 4.03 (d and m, 3H, J=14.7 Hz). 3.85 (s, 3H), 3.24 (m, 1H), 3.10–2.85 (m, 3H), 2.30 (m, 1H), 2.20 (m, 1H), 2.00–1.30 (m, 12H), 1.26(d and m, 4H, J=6.0 Hz); $^{13}$C NMR (CDCl$_3$) δ168.17, 163.44, 73.71, 73.33, 72.68, 62.19, 61.60, 58.68, 55.72, 53.58, 43.65, 42.76, 40.67, 39.07, 32.61, 30.09, 28.35, 21.80, 20.42; IR (CHCl$_3$): 3367, 1730, 1438, 1257, 1147, 1122 cm$^{-1}$; MS (m/z): 435 (MH$^+$); HRMS: Calcd for C$_{19}$H$_{30}$O$_9$S: 453.1689. Found: 435.1711.

Example 29

Preparation of Bis-lactone: A dry reaction flask equipped with a rubber septum and a magnetic stirring bar was charged with diastereoisomer 7 (26 mg, 0.067 mmol) and dry methylene chloride (5 mL) under N$_2$ at 0° C. To this solution was added a drop of trimethylsilyl trifolate and the mixture was stirred for 1 h at 0° C. and at room temperature for 2 h. The reaction progress was monitored by TLC. The reaction was quenched at 0° C. with an aqueous solution of NaHCO$_3$ (5 mL), extracted with chloroform (3×10 mL), the combined organic extracts were dried over anhydrous MgSO$_4$, and the solvent was evaporated. The resulting residue was purified by silica gel column chromatography (1% EtOH/CHCl$_3$) to afford the expected product 30 (10 mg, 44%): TLC Rf: 0.59 (10% EtOH/CHCl$_3$); $^1$H NMR (CDCl$_3$, 300 MHz) δ5.56 (m, 1H), 5.37 (m, 1H), 4.92 (m, IH), 4.30 (m, IH), 4.25 (dd, 1H, J=1.2 and 10.3 Hz), 4.01 (bd, IH, J=11.0 Hz), 3.58 (d, 1H, J=14.5 Hz), 3.29 (d, 1H, J=14.5 Hz), 2.93 (dd, 1H, J=1.9 and 16.4 Hz), 2.48 (dd, 1H, J=16.7 and 16.6 Hz), 2.40–1.90 (m, 5H), 1.80–1.40 (m, 7H), 1.21 (d, 3H, J=6.4 Hz), 1.02 (M, 1H); $^{13}$C NMR(CDCl$_3$) δ168.97, 167.52, 134.70, 130.50, 46.40, 72.15, 71.96, 44.15, 44.03, 43.00, 40.79, 37.47, 36.28, 33.33, 30.93, 25.34, 24.93, 20.38; IR (CHCl$_3$): 3407, 1692 cm$^{-1}$; CIMS (m/z): 355 (MH$^+$); HRMS: calcd for C$_{28}$H$_{26}$O$_5$S: 355.1579. found: 355.1589.

Example 30

Bis-3,5-dinitrobenzoate Derivative: A flame-dried reaction flask was charged with the Michael addition product 5 (1.75 g, 4.88 mmol), pyridine (1.94 mL) and CH$_2$Cl$_2$ (100 mL). The reaction mixture was cooled to 0° C. and to it was added 3,5-dinitrobenzoyl chloride (4.04 g, 17.56 mmol) in 5 min. under N$_2$ atmosphere. The reaction mixture was then stirred at room temperature for 24 h and quenched with a saturated aqueous solution of NaHCO$_3$ (100 mL). The resulting mixture was stirred for 10 min. and extracted with CHCl$_3$ (4×100 mL). The organic extract was washed with a saturated solution of cuss (2×100 mL) and brine (100 mL). The organic extract was dried over anhydrous MgSO$_4$ and solvent was removed under a reduced pressure. The resulting residue was purified by means of a flash column chromatography (silica gel, 1–2% EtOH/CHCl$_3$) to obtain the desired bis-3,5-dinitrobenzoate derivative 10 (1.07 g, 30%). It was recrystallized from EtOAc/n-hexanes using a solvent diffusion method. mp 110° C.; TLC Rf: 0.38 (5% EtOH/CHCl$_3$, silica gel); $^1$H NMR (CDCl$_3$, 300 MHz) δ9.24 (m, 2H), 9.18 (d, 2H, J=2.2 Hz), 9.14 (d, 2H, J=2.1 Hz), 5.69 (m, 1H), 5.48 (m, IH), 5.37 (m, 1H), 4.94 (m, IH), 4.74 (m, 1H), 4.54 (m, IH), 3.78 (dd, 1H, J=1.7 and 8.3 Hz), 3.59 (dt, IH, J=2.5 and 6.6 Hz), 3.00 (m, 2H), 2.76 (dd, 1H, J=3.7 and 16.3 Hz), 2.55–195 (m,8H), 1.90–1.55 (m, 5H), 1.27 (d, 3H, J=6.3 Hz); $^{13}$C NMR (CDCl$_3$) δ8 169.78, 162.38, 148.67, 134.779133.80,133.39, 131.46, 129.50, 129.32, 122.63, 122.34, 78.49, 71.89, 65.05, 45.81, 45.55, 44.09, 40.02, 37.16, 35.12, 33.36, 31.15, 29.22, 24.86, 20.32; IR (CHCl$_3$): 3434,2252, 1730, 1545, 1344, 1281, 1218, 1165 cm$^{-1}$.

What is claimed is:

1. A compound of the formula

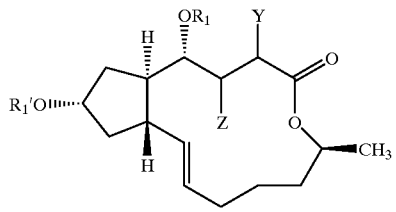

wherein $R_1$ and $R_1'$ are independently hydrogen or carboxy substituted $C_1$–$C_5$ alkanoyl, Y is H or OH, and Z is OH or —S(O)$_n$R wherein n is 0, 1 or 2 and wherein R is $C_1$–$C_6$ alkyl, phenyl, or $C_1$–$C_6$ alkyl or phenyl substituted with one or more groups selected from the group consisting of OH, $C_1$–$C_4$ alkoxy, halo, carboxy, carbo($C_1$–$C_4$ alkoxy), amino, —SO$_3$H, and mono or di ($C_1$–$C_4$ alkyl)amino, provided that when n is 0, R is not a 2-amino-2-carboxy alkyl group or an acylated derivative thereof, and provided that when Y is OH, Z is OH.

2. The compound of claim 1 wherein n=0.
3. The compound of claim 1 wherein n=1.
4. The compound of claim 1 wherein n=2.
5. A method of preparing a compound of the formula

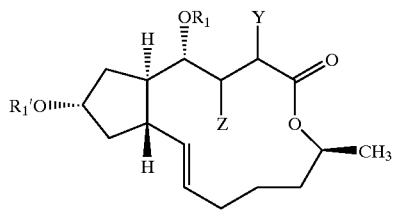

wherein $R_1$ and $R_1'$ are independently hydrogen or carboxy substituted $C_1$–$C_5$ alkanoyl, Y is H, and Z is —S(O)$_n$R wherein n is 0, 1 or 2 and wherein R is $C_1$–$C_6$ alkyl, phenyl, or $C_1$–$C_6$alkyl or phenyl substituted with one or more groups selected from the group consisting of OH, $C_1$–$C_4$ alkoxy, halo, carboxy, carbo ($C_1$–$C_4$ alkoxy), amino, —SO$_3$H, and mono or di ($C_1$–$C_4$ alkyl)amino, provided that when n is 0, R is not a 2-amino-2-carboxy alkyl group or an acylated derivative thereof, said method comprising the steps of (a) reacting brefeldin A with a thiol of the formula RSH to produce a compound of formula I wherein n is 0, and $R_1$ and $R_1'$ are hydrogen;

(b) optionally oxidizing the compound from step (a) to form a compound of formula I wherein n is 1 or 2; and, (c) optionally reacting the product of step (a) or step (b) with a $C_3$–$C_6$ cyclic anhydride to form a compound of formula I wherein at least one of $R_1$ and $R_1'$ is carboxy substituted $C_1$–$C_5$ alkanoyl.

6. A method for providing therapeutically effective serum levels of brefeldin A in a patient suffering from neoplastic disease to inhibit the growth of or to kill malignant cells in said patient, said method comprising the step of administering an effective amount of a compound of the formula

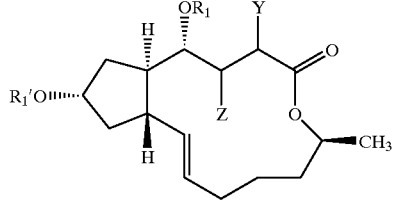

in a pharmaceutically acceptable carrier, wherein in formula I, $R_1$ and $R_1'$ are independently hydrogen or carboxy substituted $C_1$–$C_5$ akanoyl, Y is H, and Z is —S(O)$_n$R wherein n is 0 or 1 and R is $C_1$–$C_6$ alkyl, phenyl, or $C_1$–$C_6$ alkyl or phenyl substituted with one or more groups selected from the group consisting of OH, $C_1$–$C_4$ alkoxy, halo, carboxy, carbo($C_1$–$C_4$ alkoxy), amino, —SO$_3$H, and mono or di ($C_1$–$C_4$ alkyl) amino, provided that when n is 0, R is not a 2-amino-2-carboxy alkyl group or an acylated derivative thereof.

7. The method of claim 6 wherein a compound of formula I wherein n is 1 is administered.

8. The method of claim 6 wherein a compound of formula I wherein n is 0 is administered.

* * * * *